US007711163B2

(12) United States Patent
Geiger et al.

(10) Patent No.: US 7,711,163 B2
(45) Date of Patent: May 4, 2010

(54) METHOD AND SYSTEM FOR GUIDED TWO DIMENSIONAL COLON SCREENING (75) Inventors: Bernhard Geiger, Cranbury, NJ (US); Sandra Sudarsky, Bedminster, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1017 days.

(21) Appl. No.: 11/438,499

(22) Filed: May 22, 2006

(65) Prior Publication Data
US 2006/0270928 A1 Nov. 30, 2006

Related U.S. Application Data

(60) Provisional application No. 60/684,639, filed on May 26, 2005.

(51) Int. Cl.
*G06K 9/00* (2006.01)
(52) U.S. Cl. .................. 382/128; 382/131; 382/132; 382/154
(58) Field of Classification Search .................. 382/128, 382/131, 132, 154
See application file for complete search history.

(56) References Cited

U.S. PATENT DOCUMENTS

| | | | | |
|---|---|---|---|---|
| 5,260,695 | A | * | 11/1993 | Gengler et al. .............. 345/592 |
| 5,797,397 | A | * | 8/1998 | Rosenberg .................. 600/400 |
| 5,920,319 | A | * | 7/1999 | Vining et al. ............... 345/420 |
| 6,343,936 | B1 | * | 2/2002 | Kaufman et al. ............ 434/262 |
| 6,928,314 | B1 | | 8/2005 | Johnson |
| 7,352,885 | B2 | * | 4/2008 | Eberhard et al. ............ 382/131 |

FOREIGN PATENT DOCUMENTS

WO WO03077758 9/2003

OTHER PUBLICATIONS

Robb R A: "Visualization in biomedical computing" Parallel Computing, Elsevier Publishers, Amsterdam, .NL, vol. 25, No. 13-14, Dec. 1999, pp. 2067-2110, XP004363672 ISSN: 0167-8191 the whole document.
Kaufman A E et al: "Virtual colonoscopy" vol. 48, No. 2, Feb. 2005, pp. 37-41, XP002400961 ISSN: 0001-0782 cited in the application the whole document.
Macari M et al: "Comparison of time—efficient CT colonography with two—and three—dimensional colonic evaluation for detecting colorectal polyps." AJR. American Journal of Roenigenology. Jun. 2000, vol. 174, No. 6, pp. 1543-1549, XP002400962 ISSN: 0361-803X cited in the application the whole document.

(Continued)

*Primary Examiner*—Tom Y Lu
(74) *Attorney, Agent, or Firm*—Donald B. Paschburg (57) ABSTRACT

A method and system for guiding imaging reading for colon screening includes scrolling through a succession of two dimensional (2D) cross-sectional images of a colon in respective image planes. A point of intersection with a current image plane with the centerline of the colon is marked in a first color in the current cross-sectional image. As the scrolling proceeds and a new current cross-sectional image in a respective image plane is observed. a new point of intersection is marked in the current cross-sectional image in the first color and the prior point of intersection is projected onto the new current cross-sectional image and marked in a second color.

78 Claims, 4 Drawing Sheets

OTHER PUBLICATIONS

Hara A K et al: "Colorectal Polyp•Three—Dimensional Techniques" Radiology, Oak Brook,IL, US, vol. 200, No. 1, 1996, pp. 49-54, XP008027074 ISSN: 0033-8419 cited in the application the whole document.

* cited by examiner

METHOD AND SYSTEM FOR GUIDED TWO DIMENSIONAL COLON SCREENING

CROSS-REFERENCE TO RELATED APPLICATIONS AND PRIORITY

Specific reference is hereby made to Provisional Application No. 60/684,639, entitled GUIDED TWO DIMENSIONAL COLON SCREENING, filed May 26, 2005 in the names of Bernhard Geiger and Sandra Sudarsky, the inventors in the present application, and of which the benefit of priority is claimed and whereof the disclosure is hereby incorporated herein by reference in its entirety.

Reference is also made to the patent application Ser. No. 11/438,617 entitled METHOD AND SYSTEM FOR DISPLAYING UNSEEN AREAS IN GUIDED TWO DIMENSIONAL COLON SCREENING, being filed on even date herewith in the names of Bernhard Geiger and Sandra Sudarsky, the inventors in the present application, and whereof the disclosure is hereby incorporated herein by reference in its entirety.

The present application relates generally to computer vision and imaging systems and, more particularly, to computerized imaging as applied to guided two dimensional colon screening.

BACKGROUND OF THE INVENTION

Virtual colonoscopy is a noninvasive technique for human colon cancer screening. Computed tomography (CT) or Magnetic resonance (MR) techniques are used to generate high-resolution cross-sectional images of the inner surface of the colon. The techniques are presently of importance in the field of medicine Both CT and MR colonography generate a large number of images that must be interpreted by a radiologist for the presence of polyps; see Arie E. Kaufman, Sarang Lakare, Kevin Kreeger, Ingmar Bitter, Virtual Colonoscopy, Communications of the ACM, vol. 48, No. 2, pp. 37-41, 2005; and the paper by Macari, Lavelle, Berman, and Megibow cited in the next paragraph.

Commonly used methods to examine these datasets include slice-by-slice viewing, referred to as primary 2-dimensional (2D) reading and virtual flythroughs referred to as primary 3-dimensional (3D) reading. There appears to be little agreement in the literature as to which method results in the greatest rate of polyp detection; see Hara A K, Johnson C D, Reed J E, Ehman R L, Ilsrtup D M, Colorectal polyp detection with CT Colonography, two-versus three dimensional techniques, Radiology, 1996, 200:49-54; Macari M, Milano A, Lavelle M, Berman P, Megibow A J. Comparison of time-efficient CT colonography with two- and three-dimensional colonic evaluation for detecting colorectal polyps, AJR Am J Roentgenol. 2000, 174:1543-9; Macari M, Lee J, Garcia Figueiras R, Megibow A, Bennett G, Badd J, Primary 2D versus 3D Interpretation Techniques Using Thin Section Multi-Detector Row CT Colonography (CTC), RSNA, 2004.

A number of techniques have been proposed to facilitate 3D reading. Most of these techniques automate the navigation process by calculating the colonic centerline; see for example, U.S. patent application Ser. No. 10/842,972, filed May, 11, 2004 in the name of Boissonnat, Jean-Daniel and Geiger, Bernhard and entitled METHOD AND APPARATUS FOR FAST AUTOMATIC CENTERLINE EXTRACTION FOR VIRTUAL ENDOSCOPY whereof the disclosure is incorporated herein by reference; and Robert J. T. Sadleir, Paul F. Whelan , Colon Centerline Calculation for CT Colonography using Optimised 3D Topological Thinning, 1st International Symposium on 3D Data Processing Visualization and Transmission (3DPVT'02), pp. 800-804, 2002; I. Bitter, M. Sato, M. Bender, A. Kaufman, M. Wan, CEASAR: A Smooth, Accurate and Robust Centerline Extraction Algorithm, In Proc. of IEEE Visualisation, 2000; R. Chiou, A. Kaufman, Z. Liang, L. Hong, and M. Achniotou, Interactive Fly-Path Planning Using Potential Fields and Cell Decomposition for Virtual Endoscopy," IEEE Trans Nuclear Sciences, vol. 46, no. 4, pp. 1045-1049, 1999; and Samara Y, Fiebich M, Dachman A H, Kuniyoshi J K, Doi K, Hoffmann K R, Automated calculation of the centerline of the human colon on CT images, Acad Radiol. 1999 June; 6(6): 352-9;

Other techniques automate the navigation process by computing the longest ray cast along the view direction. See, for example, U.S. patent application Ser. No. 10/322,326, filed Dec. 18, 2002 in the name of B. Geiger, and entitled AUTOMATIC NAVIGATION FOR VIRTUAL ENDOSCOPY whereof the disclosure is incorporated herein by reference.

Another valuable help for 3D reading is the availability of techniques to get a map of colon wall patches that have not been observed during flythrough. Frequently, such areas are between deep Haustral folds. Such techniques have been proposed by, for example, F. M. Vos et. al. "A new visualization method for virtual colonoscopy", Lecture Notes in Computer Science, vol. 2208, 2001. However, these techniques are limited to 3D flythrough.

BRIEF SUMMARY OF THE INVENTION

It is herein recognized that very little has been proposed to facilitate slice-by-slice viewing. The convoluted structure typical of the colon makes slice-based visual inspection quite difficult. Generally, the radiologist must typically utilize manual control to browse through hundreds of two-dimensional images in search of polyps. Since the slice-based view does not provide a contiguous presentation of the inner surface of the colon, the radiologist must scroll up and down the axial images following a mental picture of the anatomical structure. An object of the present invention is to provide a method for reducing the difficulty of performing accurate slice-based visual inspection.

A basic technique for detecting colorectal polyps in CT data is to use axial images, by starting at the rectum, and carefully scrolling up and down through the images, following the colon. Since the colon is generally heavily convoluted, the scroll direction typically has to be repeatedly reversed. It is herein recognized that an important challenge for the radiologist is not to get distracted by the presence of other air filled structures in the images, such as the small intestine or other loops of the colon, which can cause pretermission or inadvertent skipping over of portions of the colon in the inspection process within which anomalies such as polyps may thus remain unobserved and undetected. Another object of the present invention is to reduce any chance of inadvertent skipping over of portions of the colon in the inspection process.

By way of an example, a colon may exhibit portions looping up and down such that an image plane may intersect the colon in a plurality of places, which will appear as more or less circular cross-sections on the image plane. Beginning at an initial point, for example at the rectal end of the colon, the radiologist can follow a series of cross-sectional images of a first ascending segment of the colon which will appear on a succession of image planes at increasing distances from the initial point. Let the first ascending segment exhibit an inverted U arch, forming a ∩-shaped segment, and continue as a descending segment. The radiologist will then see two cross-sectional images on the image plane, corresponding to the ascending and descending segments, respectively. Also, other disjoint cross-sectional images corresponding to other loops of the colon may be present on the image plane so that a total of, for example, four cross-sectional images appear on the image plane.

As the image plane scrolls up, out of the four visible cross-sectional images, the radiologist will concentrate on the ascending segment as the currently observed portion. At some point, the image plane will reach above the arch, and the cross-sectional images of the ascending and descending segments will disappear. From a knowledge of anatomy, the radiologist will understand that this is attributable to the image plane being located above the arch and that somewhere there is a continuation of the colon as the descending segment.

The image plane now scrolls down, and the radiologist must focus on the cross-sectional image of the descending segment, which is one of four cross-sectional images on the image plane. Should the radiologist through error or inadvertence at some point focus on another, incorrect cross-sectional image, a significant part might be missed, and/or valuable time lost in order to backtrack from the error. In the real world, there will typically be many more folds and the small intestine will be present in the region, which will increase the chances for error, especially for a less experienced radiologist.

In accordance with another aspect of the invention, a method provides visual feedback to assist a radiologist during the 2-D reading process in guiding the navigation procedure and to assist in focusing attention while allowing for complete control by the radiologist. The method further enables unobserved areas to be calculated and displayed. It is herein recognized that this feature has hitherto been only available for 3D flythrough. In accordance with an aspect of the invention use is made of the centerline. In accordance with another aspect of the invention no pre-calculated centerline is required.

It is known that an approximate centerline through the colon can be provided. For example, an approximate centerline can be calculated as described in the above-cited papers by J. T. Robert et al.; I. Bitter et al.; R. Chiou et al.; Y. Samara et al.; and in the above-referenced United States patent application entitled METHOD AND APPARATUS FOR FAST AUTOMATIC CENTERLINE EXTRACTION FOR VIRTUAL ENDOSCOPY.

In accordance with an aspect of the invention, a method and system for guiding imaging reading for colon screening includes scrolling through a succession of two dimensional (2D) cross-sectional images of a colon in respective image planes. A point of intersection with a current image plane with the centerline of the colon is marked in a first color in the current cross-sectional image. As the scrolling proceeds and a new current cross-sectional image in a respective image plane is observed. a new point of intersection is marked in the current cross-sectional image in the first color and the prior point of intersection is projected onto the new current cross-sectional image and marked in a second color.

In accordance with another aspect of the invention, a method comprises fading the second color in projections of prior points of intersection to a respective level, in accordance with distance from the current cross-sectional image.

In accordance with another aspect of the invention, the distance is defined in terms of sequence progression along the centerline, of the respective prior cross-sectional images from the current cross-sectional image.

In accordance with another aspect of the invention, the distance is defined in terms of Euclidean distance of the respective prior cross-sectional images from the current cross-sectional image.

In accordance with another aspect of the invention, in the event of a plurality of points of intersection of the current image with the centerline being present, marking in the second color, only that point of intersection out of the plurality exhibiting the least separation distance from the current point of intersection.

In accordance with another aspect of the invention, the separation distance is defined in terms of sequence progression along the centerline.

In accordance with another aspect of the invention, the separation distance is defined as the Euclidean distance.

In accordance with another aspect, invention comprises: scrolling to further cross-sectional images on yet further image planes and repeating the foregoing steps, mutatis mutandis; marking on each further current cross-sectional image a further current point of intersection with the centerline and marking prior points of intersection projected thereon; and if the separation distance between a projected prior point of intersection and the further current point of intersection is within a given criterion, that projected point is displayed and otherwise not.

In accordance with another aspect of the invention, the separation distance is defined in terms of sequence progression along the centerline.

In accordance with another aspect of the invention, the separation distance is defined as the Euclidean distance.

In accordance with another aspect, the invention comprises: determining the given criterion by one of: (a) user action, and (b) derivation from the distance between successive image planes.

In accordance with another aspect of the invention, the distance is defined in terms of sequence progression along the centerline.

In accordance with another aspect of the invention, the distance is defined as the Euclidean distance.

In accordance with another aspect of the invention, a method for guiding image reading for colon screening, comprises: utilizing a two dimensional (2D) image reading process for observing cross-sectional images of a colon on respective image planes; scrolling through a series of the image planes; marking, in a current cross-sectional image of a colon in a current image plane, a current point of intersection of a colon centerline and the current image plane; marking in the current cross-sectional image prior points of intersection of the centerline with respective prior image planes; marking the current point of intersection in the current cross-sectional image in a first distinctive manner; and marking the prior points of intersection in a second distinctive manner.

In accordance with another aspect of the invention, the marking the prior points of intersection comprises projecting the prior points of intersection on the current cross-sectional image.

In accordance with another aspect of the invention, the step of marking the current point of intersection comprises marking the current point in a first color; and the step of marking the prior points of intersection comprises marking the prior points in a second color.

In accordance with another aspect, the invention comprises fading the second color in the prior points of intersection to a respective level, in accordance with distance of the respective prior image planes from the current image plane.

In accordance with another aspect of the invention, the separation distance is defined in terms of sequence progression along the centerline.

In accordance with another aspect of the invention, wherein the separation distance is defined as the Euclidean distance.

In accordance with another aspect of the invention, the step of marking the prior points of intersection comprises overwriting the first color with the second color.

In accordance with another aspect of the invention, the step of marking the prior points of intersection comprises overwriting the first color with the second color pertaining to each current point of intersection that passes to becoming a prior point of intersection.

In accordance with another aspect of the invention, in the event of a plurality of points of intersection of the current image with the centerline being present, marking in the second color only that point of intersection of the plurality exhibiting the least separation between the current cross-sectional image and each respective cross-sectional image associated with each of the plurality of points of intersection.

In accordance with another aspect of the invention, the separation is defined as the Euclidean distance of the respective prior image planes from the current image plane.

In accordance with another aspect of the invention, the separation is defined in terms of sequence progression along the centerline, of the respective prior image planes from the current image plane.

In accordance with another aspect of the invention: in each successive current cross-sectional image in the scrolling, marking a respective current point of intersection in the first distinctive manner; and marking in the each successive current cross-sectional image in the scrolling, the prior points of intersection in the second distinctive manner.

In accordance with another aspect of the invention, the step of marking the current point of intersection comprises marking the current point with a first distinctive intensity modulation; and the step of marking the prior points of intersection comprises marking the prior points in a second distinctive intensity modulation.

In accordance with another aspect of the invention, the marking of the prior points of intersection comprises projecting the prior points of intersection on the current cross-sectional image.

In accordance with another aspect of the invention, a method comprises: utilizing a two dimensional (2D) image reading process for observing cross-sectional images of a colon on respective image planes; deriving a colon centerline for the colon; scrolling through a series of the image planes; marking, in a current cross-sectional image of a colon in a current image plane, a current point of intersection of the colon centerline and the current image plane; marking in the current cross-sectional image prior points of intersection of the centerline with respective priorly scrolled image planes; marking the current point of intersection in the current cross-sectional image in a first distinctive manner; and marking the prior points of intersection in a second distinctive manner.

In accordance with another aspect of the invention, a method for guiding image reading for colon screening, the method comprises: (a) deriving a colon centerline; (b) utilizing a two dimensional (2D) image reading process of observing a cross-sectional image of a colon on an image plane; (c) scrolling through a series of image plane positions by scrolling from a first image plane position looking into the colon; (d) calculating for a first current image plane position a respective first point of intersection of the centerline therewith; (e) at the first current image plane position, marking the respective first point of intersection in a first distinctive marking manner; (f) scrolling to a second image plane position as the next currently observed image plane position and making the first current image plane position a first prior image plane position; (g) overwriting the first distinctive marking manner with a second distinctive marking manner; (h) projecting the first point of intersection on the second currently observed image position; and (i) marking a second point of intersection of the centerline with the next currently observed image plane position in the first distinctive marking manner.

In accordance with another aspect of the invention, the method includes: repeating foregoing steps (b) through (i), mutatis mutandis, for successive points of intersection, scrolling to the next image plane position as the next currently observed image plane position; making the previous current image plane position a prior image plane position; and storing prior image plane positions, such that a plurality of prior image plane positions is stored.

In accordance with another aspect of the invention, a system for guiding imaging reading for colon screening, comprises: a memory device for storing a program and other data; and a processor in communication with the memory device, the processor being operative with the program to perform: utilizing a two dimensional (2D) image reading process for observing cross-sectional images of a colon on respective image planes; scrolling through a series of the image planes; marking, in a current cross-sectional image of a colon in a current image plane, a current point of intersection of a colon centerline and the current image plane; marking in the current cross-sectional image prior points of intersection of the centerline with respective prior image planes; marking the current point of intersection in the current cross-sectional image in a first distinctive manner; and marking the prior points of intersection in a second distinctive manner.

In accordance with another aspect of the invention, a computer program product comprises: a computer useable medium having computer program logic recorded thereon for program code for guiding imaging reading for colon screening, by: utilizing a two dimensional (2D) image reading process for observing cross-sectional images of a colon on respective image planes; scrolling through a series of the image planes; marking, in a current cross-sectional image of a colon in a current image plane, a current point of intersection of a colon centerline and the current image plane; marking in the current cross-sectional image prior points of intersection of the centerline with respective prior image planes; marking the current point of intersection in the current cross-sectional image in a first distinctive manner; and marking the prior points of intersection in a second distinctive manner.

In accordance with another aspect of the invention, a system for guiding imaging reading for colon screening, comprises: memory apparatus for storing a program and other data; processor apparatus for communication with the memory device, the processor apparatus being operative with the program to comprise: apparatus for utilizing a two dimensional (2D) image reading process for observing cross-sectional images of a colon on respective image planes; apparatus for scrolling through a series of the image planes; apparatus for marking, in a current cross-sectional image of a colon in a current image plane, a current point of intersection of a colon centerline and the current image plane; apparatus for marking in the current cross-sectional image prior points of intersection of the centerline with respective prior image planes; apparatus for marking the current point of intersection in the current cross-sectional image in a first distinctive manner; and apparatus for marking the prior points of intersection in a second distinctive manner.

In accordance with another aspect of the invention, a method for guiding imaging reading for colon screening comprises scrolling through a succession of two dimensional (2D) cross-sectional images of a colon in respective image planes; marking in a first color in the current cross-sectional image on a current image plane, a first point of intersection of the centerline of the colon therewith; proceeding with the scrolling to a new current cross-sectional image in a respective new current image plane; marking in the first color in the new current cross-sectional image a new point of intersection of the centerline therewith; marking a projection of the first point of intersection on the new current cross-sectional image; and marking the projection in a second color.

BRIEF DESCRIPTION OF THE SEVERAL VIEWS OF THE DRAWINGS

The invention will be more fully understood from the following detailed description, in conjunction with the drawing, not necessarily to scale, in which.

DETAILED DESCRIPTION

In the following description, functions and systems well known in the art are not set forth in detail so as to avoid cluttering and obscuring the description of the invention with unnecessary details.

Figure 1:
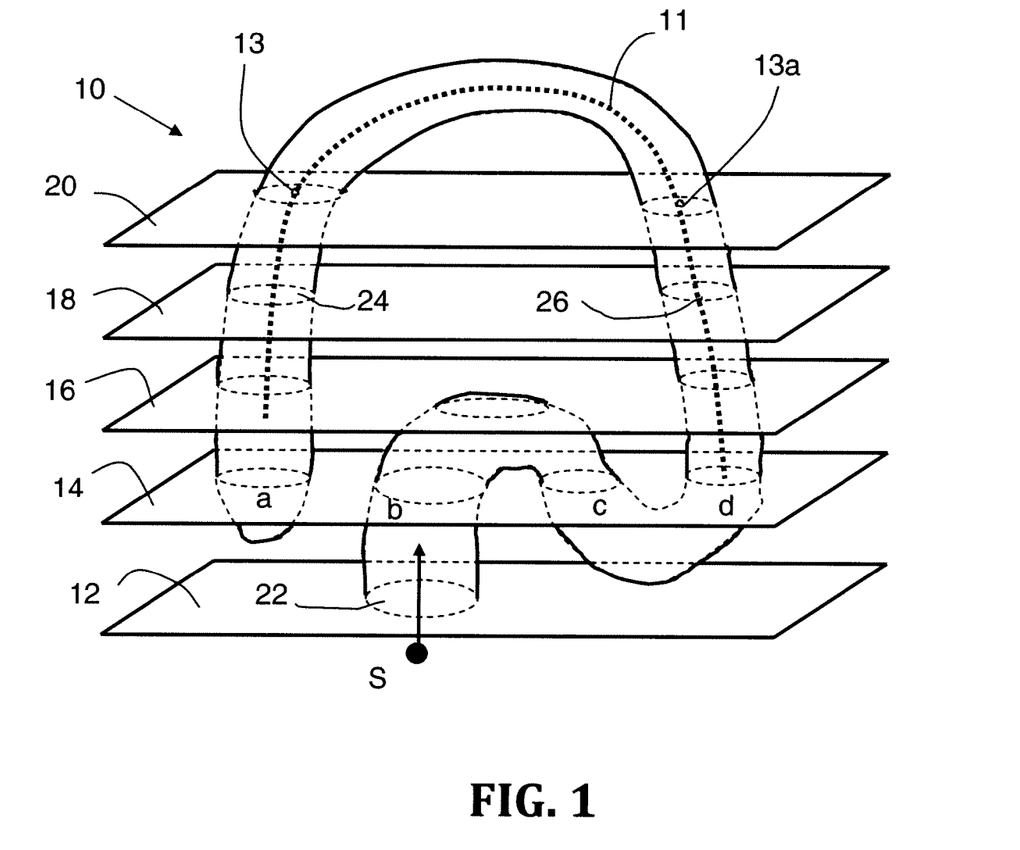
FIG. 1 shows an example of a simplified diagrammatic image of a colon, together with axial cross sections positions, helpful to gaining a fuller understanding of the present invention.

FIG. 1 shows an example of a simplified diagrammatic image of a colon 10, together with 5 axial cross sections positions, corresponding to image plane positions 12, 14, 16, 18, and 20, respectively. For convenience of explanation, a small number of equispaced discrete image plane positions with relatively wide spacing therebetween are used; however, in practice, the scrolling up and down of the image plane is performed in small overlapping increments so that the entire colon is evaluated. In this example, the radiologist, starting in an initial direction, starts at image plane position 12 at point S, then focuses on the cross-sectional image of the colon and moves the image plane up towards position 14. At that point, the radiologist will see 4 disjoint cross-sectional image areas of colon 10, marked in FIG. 1 as a, b, c, and d. The currently observed colon part is area b. As the plane of observation moves on past position 16, the area of the colon which has been is focused upon disappears. This means that the radiologist has to invert the scroll direction and move the image plane down, having to keep in mind that the observation having come from area b thus now has to follow area c. If at any position the radiologist switches focus to the wrong segment, a significant part of the colon imaging might be missed, and/or valuable time lost in order to backtrack from the error. In the real world, there will be many more folds and the small intestine will also be present, which increase the chances for error, especially for the less experienced radiologists.

Figure 2:
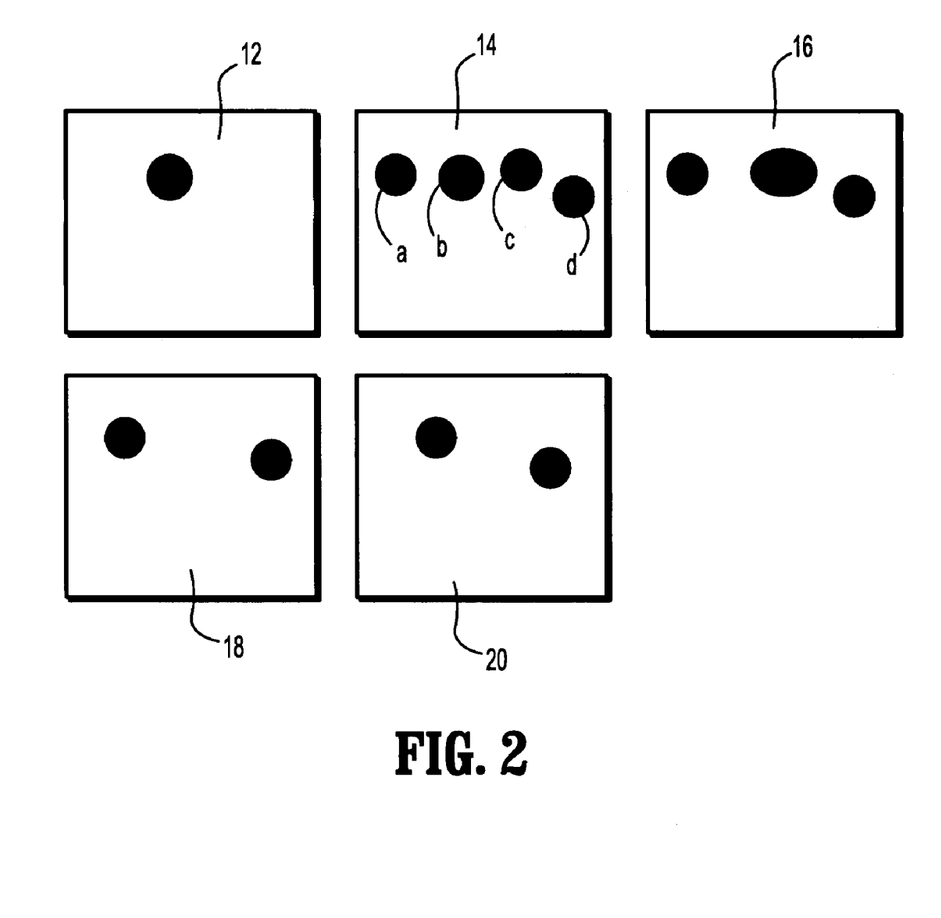
FIG. 2 shows in a simplified diagrammatic representation axial images corresponding to the constellation in FIG. 1.
Figure 3:
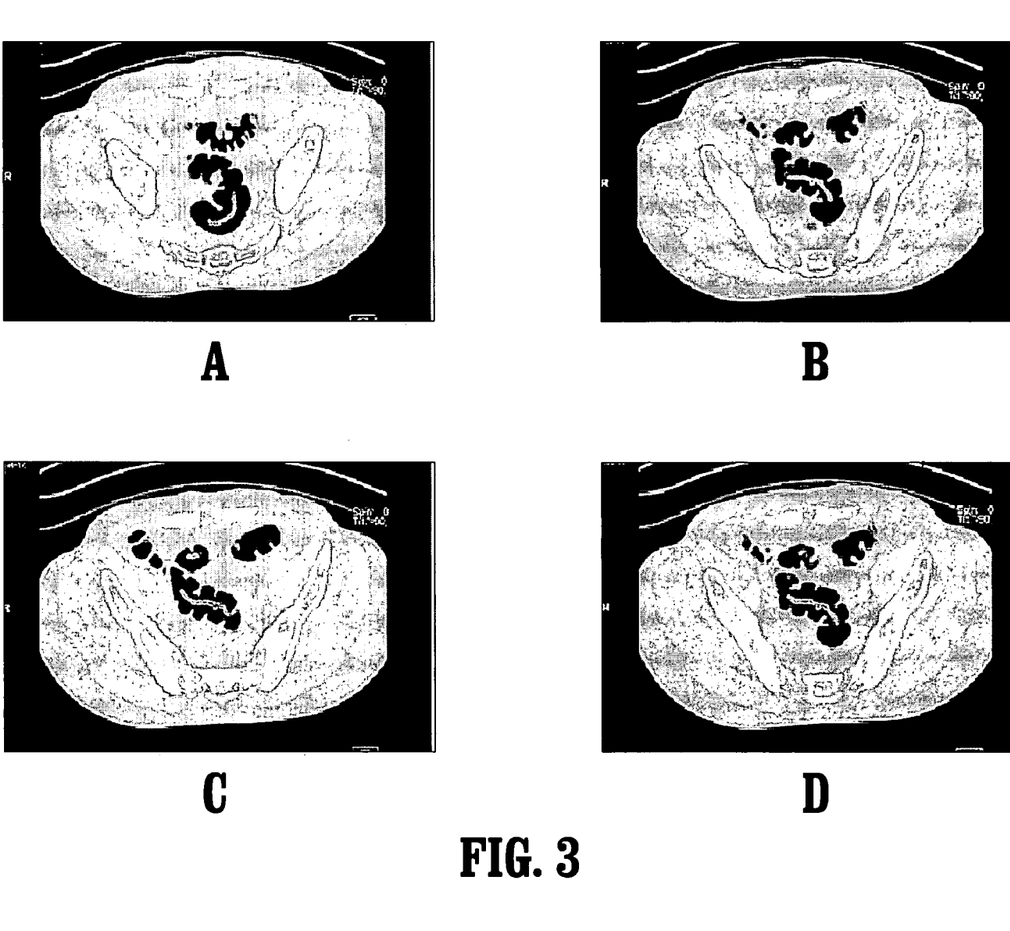
FIG. 3 shows typical operation of an exemplary embodiment in accordance with the present invention in relation to axial images of a colon.

FIG. 2 shows diagrammatically the axial cross-sectional images corresponding to the constellation of FIG. 1, wherein the numbering of each cross-section corresponds to the numbering in FIG. 1, and the parts identified by letters a, b, c, d correspond to the parts identified by the same letters in FIG. 1.

It is noted that the computed centerline is typically represented by a sequence of points that is ordered rectum to cecum or vice versa.

Let $p_0$ be the starting point of the centerline in the rectum. The process starts with an axial image looking into the colon at $p_0$. As the user moves the axial plane, the intersection of the plane with the centerline is calculated, and added to the "observed" part of the centerline. If the plane intersects at multiple or plural locations with the centerline, only the first intersection that is closest to the "observed" part will be added.

Let $\{p_0, p_1, \ldots, p_k\}$ be a sequence of 3D points representing the section of the centerline that corresponds to the portion of the colon that has already been observed. At a given instant, each point $p_i$ of the constructed centerline is projected onto the current image plane. If the distance between the projected point and $p_i$ is within a given tolerance (given by the slice thickness or user selectable), the point is displayed.

In the presently described embodiment, a straight-forward color scheme is used to display the visible centerline on top of the axial images. See the exemplary embodiment shown in FIG. 3A-FIG. 3D, which shows at different cross-sections the visible portion of the centerline superimposed onto the axial images. The red points correspond to the newly added element to the centerline and the green to previously viewed portions. A portion of the centerline is also shown diagrammatically in FIG. 1 as dotted line 11, with its intersection points 13 and 13a with plane 20.

It will be understood and borne in mind that, in accordance with typical present-day computer imaging procedures, the centerline will generally be represented by a closely-spaced series of points or dots as stated above, and these points are spaced in accordance with some convenient desired level of resolution.

Thus, in accordance with the described embodiment, the point of intersection is marked in a first color in the current image, for example red, and the previous, or preceding, points of intersection along the order of the centerline are drawn in a second color, for example, green as they appear projected into the current image plane. The second color is faded in accordance with the distance from the current image plane, in terms of the sequence progression along the centerline to the current image plane. Thus, previous points of intersection appear as corresponding points projected onto the current image plane. For controlling the fading, the distance along the centerline and/or the Euclidean distance from the current plane may be used. Use of the Euclidean distance will generally produce a longer trail if the portion of the colon is in the current plane.

This technique provides guidance during the navigation. The red point provides the focus of attention, or focus point, as one browses through the slices following the anatomical structure of the colon. If the red point is not visible, then it is also an indication that scrolling has been done in the wrong direction. The green portion provides an indication of previous path direction, with green points added most recently being the brightest and earlier added green points fading to less bright levels.

At each image, the voxels corresponding to the lumen surface containing the red dot are added to a list of observed voxels. If a segmentation of the colon is available, these observed voxels can be subtracted from the total count of surface voxels and the unobserved portion is thereby obtained. The unobserved area can be verified in a 3D view, and the virtual endoscope can be guided efficiently to each of the unobserved patches.

As was explained above in the summary of the invention, an image in the current image plane may exhibit one or more intersections with the centerline. The intersections are then sorted based on the order of progression of the centerline and the first intersection this order is taken as the focus point. The portion of the centerline that precedes the focus point is drawn in the second color, in projection on the current image plane. The intersection at the focus point is marked in the first color and the portion that succeeds the focus point is not drawn. As the user proceeds to scroll or move the cross-sectional image, the focus point will only be advanced if the intersection with the current plane is advancing in the sense of the centerline.

In the absence of a predefined centerline, the method of the present invention can still be applied by creating a centerline on the go. The creation of the centerline can be done using a combination of casting rays or growing spheres that are attached to the red dot and dragged along, always staying inside the correct lumen segment. See, for example, the aforementioned U.S. patent application Ser. No. 10/322,326 entitled AUTOMATIC NAVIGATION FOR VIRTUAL ENDOSCOPY, which discloses how to navigate without a centerline, "on the fly".

As will be understood from the foregoing, the method in accordance with the present invention supports 2D reading of colonoscopy data, by providing a visual marker that follows the lumen. Concomitant benefits and advantages include a reduced risk of missing parts, faster examination by avoiding wrong decisions, and the automatic verification of unobserved surfaces.

The method in accordance with the invention can also find an important application as a guided learning tool for less inexperienced radiologists to gain additional skills.

Figure 4:
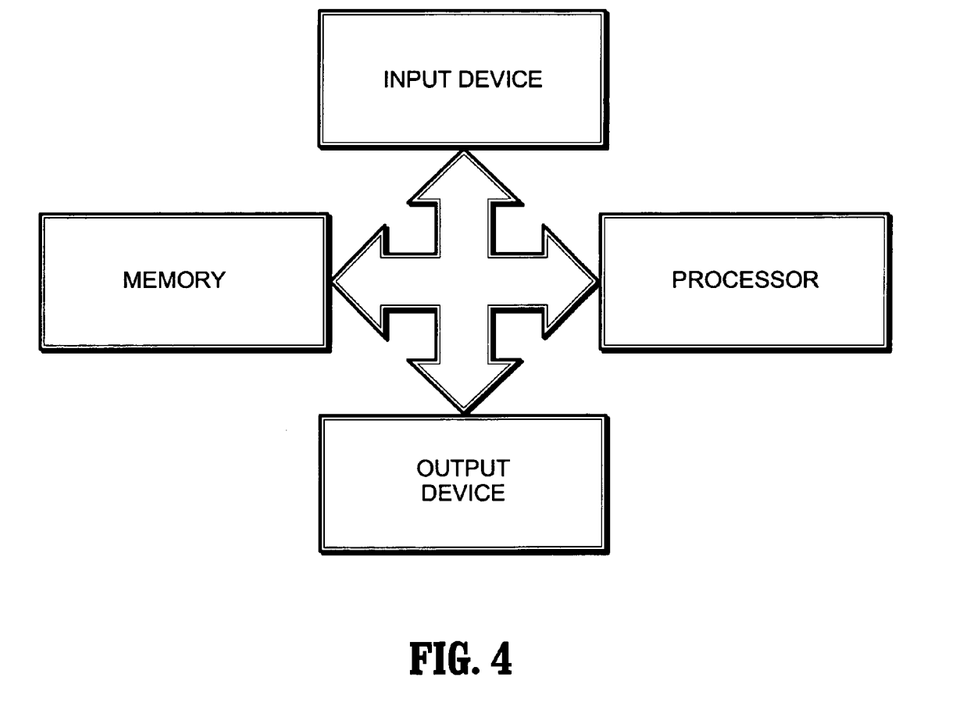
FIG. 4 shows in schematic form the application of a programmable digital computer for implementation of the invention.

As will be apparent, the present invention is best intended to be implemented with the use and application of imaging equipment in conjunction with a programmed digital computer. FIG. 4 shows in basic schematic form a digital processor coupled for two way data communication with an input device, an output device, and a memory device for storing a program and other data. The input device is so designated in broad terms as a device for providing an appropriate image or images for processing in accordance with the present invention. For example, the input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data. The output device may include a computer type display device using any suitable apparatus such as a cathode-ray kinescope tube, a plasma display, liquid crystal display, and so forth, or it may or may not include a device for rendering an image and may include a memory device or part of the memory device of FIG. 4 for storing an image for further processing, or for viewing, or evaluation, as may be convenient, or it may utilize a connection or coupling including such as are noted above in relation to the input device. The processor is operative with a program set up in accordance with the present invention for implementing steps of the invention. Such a programmed computer may interface readily through communications media such as land line, radio, the Internet, and so forth for image data acquisition and transmission.

Images may be inputted directly, or by way of storage, or communication with another computer or device by way of direct connection, a modulated infrared beam, radio, land line, facsimile, or satellite as, for example, by way of the World Wide Web or Internet, or any other appropriate source of such data. The image output device may include a computer type display device using any suitable apparatus such as a cathode-ray kinescope tube, a plasma display, liquid crystal display, and so forth, or it may include memory for storing an image for further processing, or for viewing, or evaluation, as may be convenient, or it may utilize a connection or coupling including such as are noted above in relation to the input. The processor is operative with a program set up in accordance with the present invention for implementing steps of the invention. Such a programmed computer may interface readily through communications media such as land line, radio, the Internet, and so forth for image data acquisition and transmission.

The invention may be readily implemented, at least in part, in a software memory device and packaged in that form as a software product. This can be in the form of a computer program product comprising a computer useable medium having computer program logic recorded thereon for program code for performing the method of the present invention.

The present invention has also been explained in part by way of examples using illustrative exemplary embodiments. It will be understood that the description by way of exemplary embodiments is not intended to be limiting and that, while the present invention is broadly applicable, it is helpful to also illustrate its principles, without loss of generality, by way of exemplary embodiments relating to an important field of application for the present invention, namely, to computer vision and imaging systems and, more particularly, to computerized imaging as applied to guided two dimensional colon screening.

It will also be understood that various changes and substitutions not necessarily herein explicitly described may be made by one of skill in the art to which it pertains. In the present exemplary embodiments, axial images have been used to simplify the description; however, the present invention is also applicable to coronal images, sagittal images, and images on oblique planes. Thus, for example, the distinctive marking on previously observed images and on the current image being observed in exemplary embodiments are in terms of distinctive colors, such as green and red. Other distinctive markings, such as intensity variation or modulation, pulsing and so forth are possible. These and similar changes and substitutions may be made without departing from the spirit and scope of the invention which is defined by the claims following.

What is claimed is:

1. A method for guiding imaging reading for colon screening comprising:

scrolling through a succession of two dimensional (2D) cross-sectional images of a colon in respective image planes;

marking in a first color in the current cross-sectional image on a current image plane, a first point of intersection of the centerline of the colon therewith;

proceeding with said scrolling to a new current cross-sectional image in a respective new current image plane;

marking in said first color in said new current cross-sectional image a new point of intersection of said centerline therewith;

marking a projection of said first point of intersection on said new current cross-sectional image; and marking said projection in a second color.

2. A method as recited in claim 1, comprising:
fading said second color in projections of prior points of intersection to a respective level, in accordance with distance from said current cross-sectional image.

3. A method as recited in claim 2, wherein said distance is defined in terms of sequence progression along said centerline, of said respective prior cross-sectional images from said current cross-sectional image.

4. A method as recited in claim 2, wherein said distance is defined in terms of Euclidean distance of said respective prior cross-sectional images from said current cross-sectional image.

5. A method as recited in claim 1 wherein:
in the event of a plurality of points of intersection of said new current image plane with said centerline being present, marking in said first color, only that point of intersection out of said plurality exhibiting the least separation distance from said first point of intersection.

6. A method as recited in claim 5, wherein said separation distance is defined in terms of sequence progression along said centerline.

7. A method as recited in claim 5, wherein said separation distance is defined as the Euclidean distance.

8. A method as recited in claim 1, comprising:
scrolling to further cross-sectional images on yet further image planes and repeating the foregoing steps, mutatis mutandis;
marking on each further current cross-sectional image a further current point of intersection with said centerline and marking prior points of intersection projected thereon; and
if the separation distance between a projected prior point of intersection and said further current point of intersection is within a given criterion, that projected point is displayed and otherwise not.

9. A method as recited in claim 8, wherein said separation distance is defined in terms of sequence progression along said centerline.

10. A method as recited in claim 8, wherein said separation distance is defined as the Euclidean distance.

11. A method as recited in claim 8, comprising:
determining said given criterion by one of:
(a) user action, and
(b) derivation from the distance between successive image planes.

12. A method as recited in claim 11, wherein said distance is defined in terms of sequence progression along said centerline.

13. A method as recited in claim 11, wherein said distance is defined as the Euclidean distance.

14. A method for guiding imaging reading for colon screening, said method comprising:
scrolling through a succession of two dimensional (2D) cross-sectional images of a colon in respective image planes including a current cross-sectional image in a current image plane;
marking in a first color on said current image plane a current point of intersection therewith of a centerline of said colon; and
marking in a second color on said current image plane projections of prior points of intersection of said centerline with respective image planes of prior cross-sectional images.

15. A method as recited in claim 14, comprising:
fading said second color in said prior points of intersection to a respective level, in accordance with distance of said respective prior cross-sectional images from said current cross-sectional image.

16. A method as recited in claim 15, wherein said distance is defined in terms of sequence progression along said centerline.

17. A method as recited in claim 15, wherein said distance is defined as the Euclidean distance.

18. A method as recited in claim 14 wherein:
in the event of a plurality of points of intersection of said current image plane with said centerline being present, marking in said second color, only that point of intersection out of said plurality exhibiting the least separation from said current point of intersection.

19. A method as recited in claim 18, wherein said separation is defined in terms of sequence progression along said centerline.

20. A method as recited in claim 15, comprising:
scrolling to further cross-sectional images on yet further image planes and repeating the foregoing steps, mutatis mutandis;
marking on each further current image plane a further current point of intersection with said centerline and marking prior points of intersection projected thereon; and
if the separation distance between a projected prior point of intersection and said further current point of intersection is within a given criterion, then displaying that projected point and otherwise not.

21. A method as recited in claim 20, wherein said separation distance is defined in terms of sequence progression along said centerline.

22. A method as recited in claim 20, wherein said separation distance is defined as the Euclidean distance.

23. A method as recited in claim 20, comprising:
determining said given criterion by one of:
(a) user action, and
(b) derivation from the distance between successive image planes.

24. A method as recited in claim 23, wherein:
said separation distance is measured in terms of sequence progression along said centerline.

25. A method as recited in claim 23, wherein said separation distance is defined as the Euclidean distance.

26. A method for guiding image reading for colon screening, said method comprising:
utilizing a two dimensional (2D) image reading process for observing cross-sectional images of a colon on respective image planes;
scrolling through a series of said image planes;
marking, in a current image plane, a current point of intersection of a colon centerline and said current image plane;
marking in said current image plane projections of prior points of intersection of said centerline with respective prior image planes;
marking said current point of intersection in said current image plane in a first distinctive manner; and
marking said projections of prior points of intersection in a second distinctive manner.

27. A method as recited in claim 26, wherein:
said step of marking said current point of intersection comprises marking said current point in a first color; and said step of marking said projections of prior points of intersection comprises marking said projections of prior points in a second color.

28. A method as recited in claim 27, comprising:
fading said second color in said projections of prior points of intersection to a respective level, in accordance with a separation distance of said respective prior image planes from said current image plane.

29. A method as recited in claim 28, wherein said separation distance is defined in terms of sequence progression along said centerline.

30. A method as recited in claim 28, wherein said separation distance is defined as the Euclidean distance.

31. A method as recited in claim 27, wherein:
said step of marking said prior points of intersection comprises overwriting said first color with said second color.

32. A method as recited in claim 27, including a step of:
marking said prior points of intersection by overwriting said first color with said second color pertaining to each current point of intersection that passes to becoming a prior point of intersection.

33. A method as recited in claim 27 wherein:
in the event of a plurality of points of intersection of said current image plane with said centerline being present, marking in said second color only that point of intersection of said plurality exhibiting the least separation between said current cross-sectional image and each respective cross-sectional image associated with each of said plurality of points of intersection.

34. A method as recited in claim 33, wherein said separation is defined as the Euclidean distance of said respective prior image planes from said current image plane.

35. A method as recited in claim 33, wherein said separation is defined in terms of sequence progression along said centerline, of said respective prior image planes from said current image plane.

36. A method as recited in claim 26, comprising:
in each successive current cross-sectional image in said scrolling, marking a respective current point of intersection in said first distinctive manner; and
marking in said each successive current cross-sectional image in said scrolling, said projections of prior points of intersection in said second distinctive manner.

37. A method as recited in claim 36, wherein:
said step of marking said current point of intersection comprises marking said current point with a first distinctive intensity modulation; and
said step of marking said projections of prior points of intersection comprises marking said projections of prior points in a second distinctive intensity modulation.

38. A method for guiding image reading for colon screening, said method comprising:
utilizing a two dimensional (2D) image reading process for observing cross-sectional images of a colon on respective image planes;
deriving a colon centerline for said colon;
scrolling through a series of said image planes;
marking, in a current image plane, a current point of intersection of said colon centerline and said current image plane;
marking in said current image plane projections of prior points of intersection of said centerline with respective priorly scrolled image planes;
marking said current point of intersection in said current image plane in a first distinctive manner; and
marking said projections of prior points of intersection in a second distinctive manner.

39. A method as recited in claim 38, wherein:
said step of marking said current point of intersection comprises marking said current point in a first distinctive color; and
said step of marking said projections of prior points of intersection comprises marking said projections of prior points in a second distinctive color.

40. A method as recited in claim 39 wherein:
in the event of a plurality of points of intersection of said current image plane with said centerline being present, marking in said second color only that point of intersection of said plurality exhibiting the least separation between said current cross-sectional image and each respective cross-sectional image associated with each of said plurality of points of intersection.

41. A method as recited in claim 40 wherein said separation is defined as at least one of distance in terms of sequence progression along said centerline and Euclidean distance.

42. A method as recited in claim 39, comprising:
fading said second distinctive color in each successive current cross-sectional image such that said fading at each of said prior points is in accordance with the separation between said current cross-sectional plane and the respective cross-sectional plane corresponding to each of said prior points.

43. A method as recited in claim 42, wherein said separation is defined as Euclidean distance.

44. A method as recited in claim 42, wherein said separation corresponds to scrolling order separation in said scrolling.

45. A method as recited in claim 42 wherein said separation is defined as at least one of distance in terms of sequence progression along said centerline and Euclidean distance 46. A method as recited in claim 39, wherein:
said step of marking said projections of said prior points of intersection comprises overwriting said first distinctive color with said second distinctive color.

47. A method as recited in claim 39, wherein:
said step of marking said projections of prior points of intersection comprises overwriting said first distinctive color with said second distinctive color pertaining to each current point of intersection that passes to becoming a prior point of intersection.

48. A method as recited in claim 38, comprising:
in each successive current cross-sectional image in said scrolling, marking a respective current point of intersection in said first distinctive manner; and
marking in said each successive current image in said scrolling, said projections of said prior points of intersection in said second distinctive manner.

49. A method as recited in claim 40, wherein:
said step of marking said current point of intersection comprises marking said current point with a first distinctive intensity modulation; and
said step of marking said prior points of intersection comprises marking said prior points in a second distinctive intensity modulation.

50. A method as recited in claim 40, comprising:
fading said second distinctive color in accordance with the distance of said respective portions of said centerline from said current image.

51. A method as recited in claim 50, wherein said distance is defined in terms of sequence progression along said centerline.

52. A method as recited in claim 50, wherein said distance is defined as the Euclidean distance.

53. A method as recited in claim 40, comprising:
overwriting with a second distinctive color said current portion of said centerline in said current cross-sectional image, currently colored in said first distinctive color, when a succeeding cross-section becomes the current cross-sectional image.

54. A method as recited in claim 38 comprising:
in the event of a plurality of points of intersection of said current image plane with said centerline being present, marking in said first distinctive manner only that portion of said centerline corresponding to a point of intersection of said plurality which is closest to said current cross-sectional image.

55. A method for guiding image reading for colon screening, said method comprising:
(a) deriving a colon centerline;
(b) utilizing a two dimensional (2D) image reading process of observing a cross-sectional image of a colon on an image plane;
(c) scrolling through a series of image plane positions by scrolling from a first image plane position looking into said colon;
(d) calculating for a first current image plane position a respective first point of intersection of said centerline therewith;
(e) at said first current image plane position, marking said respective first point of intersection in a first distinctive marking manner;
(f) scrolling to a second image plane position as the next currently observed image plane position and making said first current image plane position a first prior image plane position;
(g) overwriting said first distinctive marking manner with a second distinctive marking manner;
(h) projecting said first point of intersection on said second currently observed image position; and
(i) marking a second point of intersection of said centerline with said next currently observed image plane position in said first distinctive marking manner.

56. A method as recited in claim 55, comprising:
repeating foregoing steps (b) through (i), mutatis mutandis, for successive points of intersection, scrolling to the next image plane position as the next currently observed image plane position;
making the previous current image plane position a prior image plane position; and
storing prior image plane positions, such that a plurality of prior image plane positions is stored.

57. A method as recited in claim 56, wherein:
in step (e) said marking in a first distinctive marking manner comprises marking in a first distinctive color; and
in step (i) said overwriting with a second distinctive marking manner comprises marking in a second distinctive color.

58. A method as recited in claim 57, comprising:
fading said second distinctive color such that a respective degree of fading at each associated point of intersection of said prior points is in accordance with distance from the current image plane position of a respective prior image plane position containing said associated point of intersection.

59. A method as recited in claim 58, wherein said distance is defined in terms of sequence progression along said centerline.

60. A method as recited in claim 58, wherein said distance is defined as the Euclidean distance of said respective prior image planes from said current image plane.

61. A method as recited in claim 55, wherein, in the event said next image plane position intersects said centerline at a plurality of points of intersection, then
selecting out of said plurality as said second point of intersection that which exhibits the closest distance to said first point of intersection, measured in terms of sequence progression along said centerline.

62. A method as recited in claim 61, wherein said distance is defined as the Euclidean distance of said respective prior image planes from said current image plane.

63. A method as recited in claim 61, wherein said distance is defined in terms of sequence progression along said centerline, of said respective prior image planes from said current image plane.

64. A method as recited in claim 55, comprising:
scrolling to yet further cross-sectional images on yet further image planes and repeating the foregoing steps, mutatis mutandis;
projecting foregoing points of intersection on each successive current image plane; and
if the separation distance between a projected point and the current point of intersection is within a given criterion, that projected point is displayed and otherwise not.

65. A method as recited in claim 64, wherein said separation distance is defined in terms of sequence progression along said centerline.

66. A method as recited in claim 64, wherein said separation distance is defined as the Euclidean distance.

67. A method as recited in claim 64, comprising:
determining said given criterion by one of:
(a) user action, and
(b) derivation from the distance between successive image planes.

68. A method as recited in claim 64, wherein:
said distance is measured in terms of sequence progression along said centerline.

69. A method as recited in claim 64, wherein said separation distance is defined as Euclidean distance.

70. A system for guiding imaging reading for colon screening, comprising:
a memory device for storing a program and other data;
a processor in communication with said memory device, said processor is operative with said program to perform:
utilizing a two dimensional (2D) image reading process for observing cross-sectional images of a colon on respective image planes;
scrolling through a series of said image planes;
marking, in a current cross-sectional image of a colon in a current image plane, a current point of intersection of a colon centerline and said current image plane;
marking in said current image plane respective projections of prior points of intersection of said centerline with respective prior image planes;
marking said current point of intersection in said current image plane in a first distinctive manner; and
marking said respective projections of prior points of intersection in a second distinctive manner.

71. A system in accordance with claim 70, wherein said processor is operative with said program to perform:
said marking said prior points of intersection comprising projecting said prior points of intersection on said current image plane.

72. A system in accordance with claim 71, wherein said processor is operative with said program to perform:
said step of marking said current point of intersection comprising marking said current point in a first color; and said step of marking said respective projections of prior points of intersection comprising marking said respective projections of prior points in a second color.

73. A system in accordance with claim 72, wherein said processor is operative with said program to perform:

fading said second color in said respective projections of prior points of intersection to a respective level, in accordance with distance of said respective prior image planes from said current image plane.

74. A computer program product comprising:

a computer useable medium having computer program logic recorded thereon for program code for guiding imaging reading for colon screening, by programming said computer for:

utilizing a two dimensional (2D) image reading process for observing cross-sectional images of a colon on respective image planes;

scrolling through a series of said image planes;

marking, in a current image plane of a colon in a current image plane, a current point of intersection of a colon centerline and said current image plane;

marking in said current image plane respective projections of prior points of intersection of said centerline with respective prior image planes;

marking said current point of intersection in said current image plane in a first distinctive manner; and marking said respective projections of prior points of intersection in a second distinctive manner.

75. A computer program product in accordance with claim 74, wherein said processor is operative with said program to perform:

said marking said prior points of intersection comprises projecting said prior points of intersection on said current image plane.

76. A computer program product in accordance with claim 75, wherein said processor is operative with said program to perform:

said step of marking said current point of intersection comprising marking said current point in a first color; and said step of marking said prior points of intersection comprising marking said prior points in a second color.

77. A computer program product in accordance with claim 76, wherein said processor is operative with said program to perform:

fading said second color in said prior points of intersection to a respective level, in accordance with distance of said respective prior image planes from said current image plane.

78. A system for guiding imaging reading for colon screening, comprising:

memory means for storing a program and other data;

processor means for communication with said memory device, said processor means being operative with said program to comprise:

means for utilizing a two dimensional (2D) image reading process for observing cross-sectional images of a colon on respective image planes;

means for scrolling through a series of said image planes;

means for marking, in a current cross-sectional image of a colon in a current image plane, a current point of intersection of a colon centerline and said current image plane;

means for marking in said current image plane projections of prior points of intersection of said centerline with respective prior image planes;

means for marking said current point of intersection in said current image plane in a first distinctive manner; and means for marking said projections of prior points of intersection in a second distinctive manner.

* * * * *